(12) United States Patent
Starr et al.

(10) Patent No.: US 11,674,943 B2
(45) Date of Patent: *Jun. 13, 2023

(54) METHOD AND APPARATUS FOR ROBOTIC, IN-PIPE WATER QUALITY TESTING

(71) Applicant: RedZone Robotics, Inc., Warrendale, PA (US)

(72) Inventors: Justin Starr, Baden, PA (US); John Lettman, Pittsburgh, PA (US); Todd Kueny, Tarentum, PA (US); Foster J. Salotti, Verona, PA (US); Galin Konakchiev, Pittsburgh, PA (US)

(73) Assignee: RedZone Robotics, Inc., Warrendale, PA (US)

( * ) Notice: Subject to any disclaimer, the term of this patent is extended or adjusted under 35 U.S.C. 154(b) by 295 days.

This patent is subject to a terminal disclaimer.

(21) Appl. No.: 17/086,361

(22) Filed: Oct. 31, 2020

(65) Prior Publication Data

US 2021/0048423 A1 Feb. 18, 2021

Related U.S. Application Data

(63) Continuation of application No. 16/429,655, filed on Jun. 3, 2019, now Pat. No. 10,859,554, which is a continuation of application No. 15/278,924, filed on Sep. 28, 2016, now Pat. No. 10,309,949.

(51) Int. Cl.
*G01N 33/18* (2006.01)
*F16L 55/34* (2006.01)
*G01S 15/88* (2006.01)
*G01S 17/88* (2006.01)
*F16L 101/30* (2006.01)

(52) U.S. Cl.
CPC .......... *G01N 33/1886* (2013.01); *F16L 55/34* (2013.01); *G01N 33/1813* (2013.01); *F16L 2101/30* (2013.01); *G01S 15/88* (2013.01); *G01S 17/88* (2013.01); *Y10S 901/01* (2013.01); *Y10S 901/44* (2013.01)

(58) Field of Classification Search
None
See application file for complete search history.

(56) References Cited

U.S. PATENT DOCUMENTS 8,024,066 B2 * 9/2011 Reverte ................ G01S 13/881 385/103
8,041,517 B2 * 10/2011 Thayer .................... E21B 47/00 702/33

(Continued)

*Primary Examiner* — Daniel S Larkin
(74) *Attorney, Agent, or Firm* — Gabriel & Co; Andrew M Gabriel

(57) ABSTRACT

One embodiment provides a pipe inspection robot, including: a chassis configured to traverse through an interior of a water or sewer pipe; a water quality probe comprising a first end that couples to the chassis and a sensing end distal thereto; an electric motor configured to reposition the sensing end of the water quality probe with respect to the chassis; said electric motor acting to move the sensing end of the water quality probe to reposition the sensing end proximate to fluid containing water located proximate to a bottom part of the chassis; the sensing end configured to contact the fluid containing water for contact sensing of water quality data. Other aspects are described and claimed.

20 Claims, 4 Drawing Sheets

(56) References Cited

U.S. PATENT DOCUMENTS

| | | | | |
|---|---|---|---|---|
| 8,138,471 B1* | 3/2012 | Shedlock | ............... | G01V 5/08 |
| | | | | 250/269.1 |
| 8,479,598 B2* | 7/2013 | Vincent | ............. | G01N 33/1886 |
| | | | | 73/866.5 |
| 8,525,124 B2* | 9/2013 | Atwood | ................ | G01N 35/00 |
| | | | | 356/241.6 |
| 8,805,579 B2* | 8/2014 | Skrinde | ............... | B25J 11/0085 |
| | | | | 134/18 |
| 10,309,949 B2* | 6/2019 | Starr | ................ | G01N 33/1886 |
| 2010/0191376 A1* | 7/2010 | Close | .................... | B25J 9/1617 |
| | | | | 700/259 |
| 2012/0197440 A1* | 8/2012 | Farkavec | ............... | B08B 9/049 |
| | | | | 901/1 |

\* cited by examiner

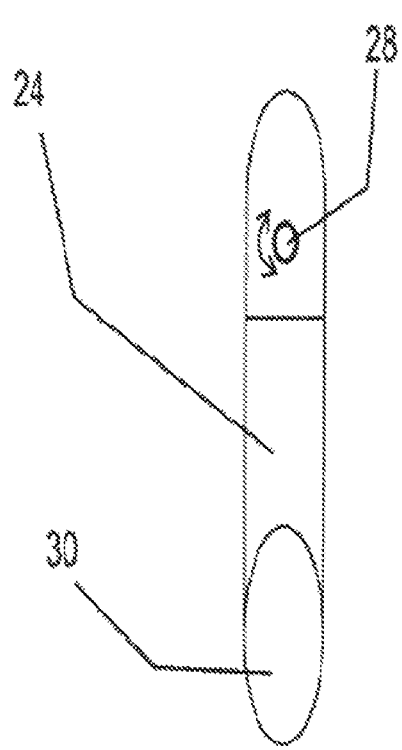
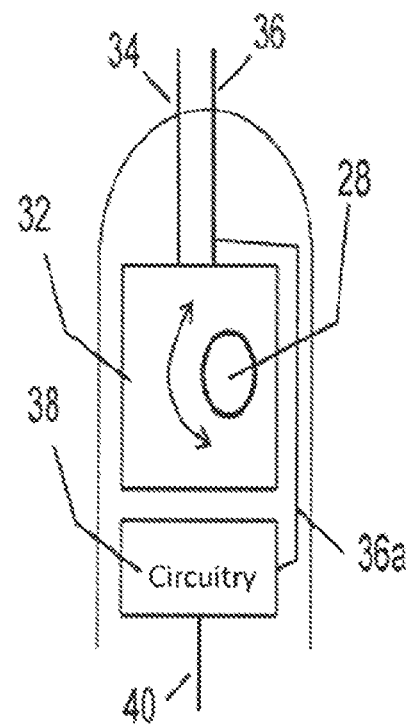
FIG. 2A
FIG. 2B

METHOD AND APPARATUS FOR ROBOTIC, IN-PIPE WATER QUALITY TESTING

CROSS-REFERENCE TO RELATED APPLICATIONS

This application is a continuation application of U.S. application Ser. No. 16/429,655, filed on Jun. 3, 2019, now U.S. Pat. No. 10,859,554, and U.S. application Ser. No. 15/278,924 filed on Sep. 28, 2016, now U.S. Pat. No. 10,309,949, the contents of which are incorporated by reference in their entirety herein.

BACKGROUND

Measuring water quality in a pipe system, e.g., a pipe carrying water treatment facility inflow or outflow, a sewer system, etc., is often a difficult and time-consuming task. Conventionally, water samples must be collected and taken to a lab where each characteristic of interest is measured.

There are sensing elements, e.g., pH probes, dissolved oxygen probes, oxidation-reduction potential (ORP) probes, and the like, that detect pH, dissolved oxygen, heavy metals, etc., based on contact with a test fluid. Such probes work well and can return results as soon as they contact the fluid.

Conventionally, contact based probes are manually placed into contact with the water or fluid of interest. This involves a human being taking the probe and locating it in contact with the fluid. In some cases, e.g., in sealed pipes, the probe can be mounted in a port of the wall of the pipe and monitor the fluid content thereof. In other cases, humans take a sample of fluid and bring it in to contact with the probes at a later time.

BRIEF SUMMARY

In summary, one aspect provides a pipe inspection robot, comprising: a chassis configured to traverse through an interior of a water or sewer pipe; a water quality probe comprising a first end that couples to the chassis and a sensing end distal thereto; an electric motor configured to reposition the sensing end of the water quality probe with respect to the chassis; said electric motor acting to move the sensing end of the water quality probe to reposition the sensing end proximate to fluid containing water located proximate to a bottom part of the chassis; the sensing end configured to contact the fluid containing water for contact sensing of water quality data.

Another aspect provides a method for obtaining water quality data for a fluid containing water within a pipe, comprising: positioning a pipe inspection robot within a pipe; collecting, using a water quality probe of the pipe inspection robot, water quality data; the collecting comprising operating an electric motor to reposition a sensing end of the water quality probe with respect to the robot; said electric motor acting to move the sensing end of the water quality probe to reposition the sensing end proximate to fluid containing water located proximate to a bottom part of the pipe inspection robot; the sensing end contacting the fluid containing water for contact sensing of water quality data; and communicating, over a network connection, the water quality data to a remote device.

A further aspect provides a pipe inspection robot, comprising: a chassis; a water quality probe coupled to the chassis; an electric motor that imparts movement to the water quality probe to reposition the water quality probe to a position that is closer to a bottom part of the chassis; wherein, in the position, a sensing end of the water quality probe is able to contact fluid comprising water located in a bottom of the pipe proximate to a bottom of the chassis; and a processor operatively coupled to the water quality probe; said processor configured to: operate the water quality probe to collect water quality data related to the fluid comprising water contained within the pipe; and communicate the water quality data collected over a network connection.

The foregoing is a summary and thus may contain simplifications, generalizations, and omissions of detail; consequently, those skilled in the art will appreciate that the summary is illustrative only and is not intended to be in any way limiting.

For a better understanding of the embodiments, together with other and further features and advantages thereof, reference is made to the following description, taken in conjunction with the accompanying drawings. The scope of the invention will be pointed out in the appended claims.

BRIEF DESCRIPTION OF THE SEVERAL VIEWS OF THE DRAWINGS

FIG. 2(A-B) illustrates example views of a water quality probe.

DETAILED DESCRIPTION

Figure 1:
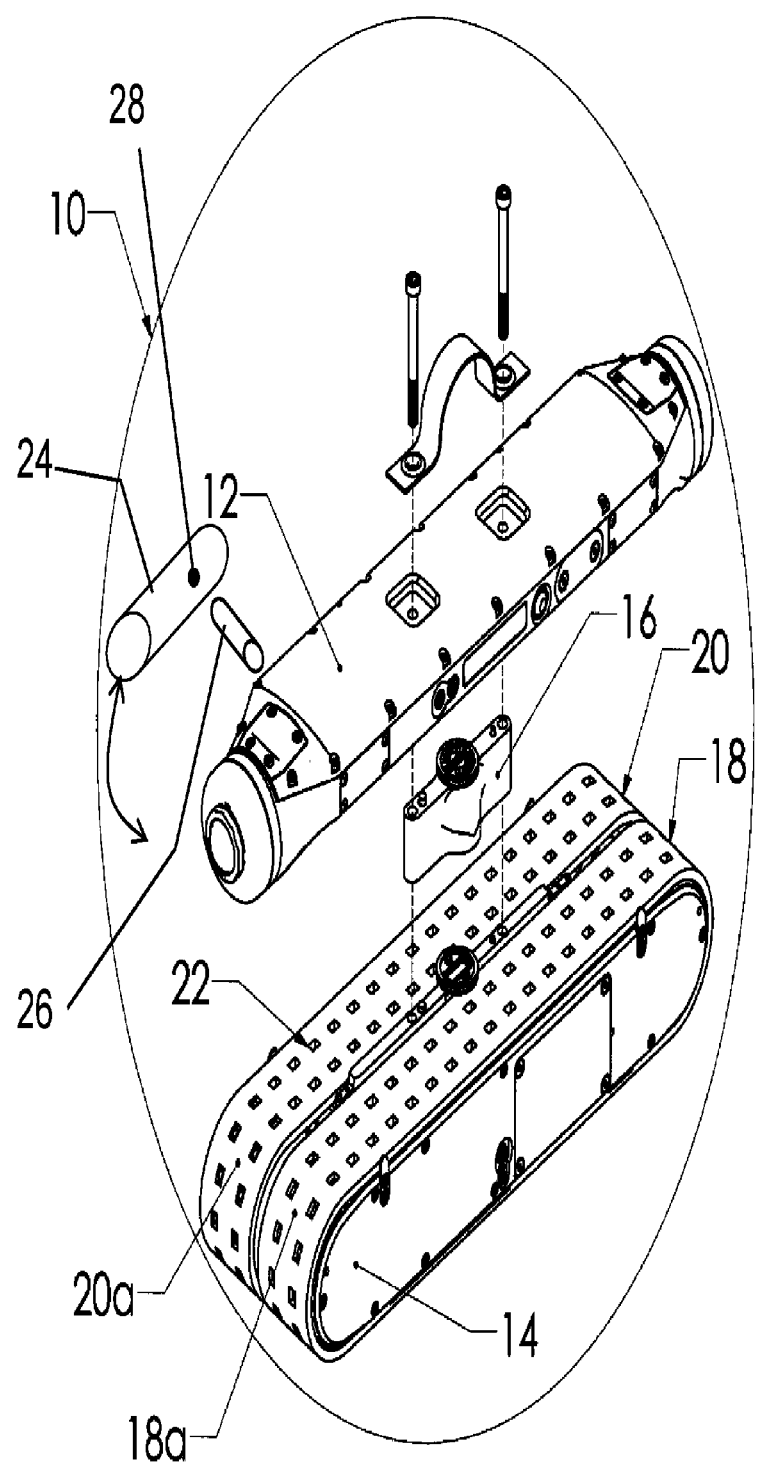
FIG. 1 illustrates an example pipe inspection robot.

It will be readily understood that the components of the embodiments, as generally described and illustrated in the figures herein, may be arranged and designed in a wide variety of different configurations in addition to the described example embodiments. Thus, the following more detailed description of the example embodiments, as represented in the figures, is not intended to limit the scope of the embodiments, as claimed, but is merely representative of example embodiments.

Reference throughout this specification to "embodiment(s)" (or the like) means that a particular feature, structure, or characteristic described in connection with the embodiment is included in at least one embodiment. Thus, appearances of the phrases "according to embodiments" or "an embodiment" (or the like) in various places throughout this specification are not necessarily all referring to the same embodiment.

Furthermore, the described features, structures, or characteristics may be combined in any suitable manner in one or more embodiments. In the following description, numerous specific details are provided to give a thorough understanding of embodiments. One skilled in the relevant art will recognize, however, that the various embodiments can be practiced without one or more of the specific details, or with other methods, components, materials, etc. In other instances, well known structures, materials, or operations are not shown or described in detail to avoid obfuscation.

In some cases, e.g., in a subterranean sewer pipe, manual collection of samples, manual insertion of contact-based sensors, and/or placement or mounting of dedicated sensors is extremely inconvenient, impossible, or cost-prohibitive. This leads to either a complete lack of water quality testing or results in infrequent water quality testing in such environments.

An embodiment provides a mobile pipe inspection robot that has integrated therewith one or more probes for water quality analysis to provide real-time information about the characteristics of a stream of effluent. The probe(s) comprise one or more sensors that sense water quality characteristics, e.g., dissolved oxygen, pH, heavy metals, ORP, etc. The data from the probe(s) may be reported by the mobile pipe inspection robot in a variety of way s.

For example, in an embodiment, the probe data is used to overlay information about water quality on a video feed provided by the mobile pipe inspection robot, e.g., a video of the pipe interior. As another example, the probe data is used in a targeted fashion to determine the temperature and makeup of an incoming illegal or unauthorized discharge or inflow into a sewer pipe. Results that are of interest, e.g., fluid pH, are immediately displayed via a live feed and a complete report showing quality varying with inspection time is produced to help clients pinpoint illegal or unauthorized discharges or inflows.

An embodiment permits the collecting of these readings continuously throughout the survey. Thus, there may not be just one pH measurement, but a plot of time vs. pH for the duration of the inspection.

The description now turns to the figures. The illustrated example embodiments will be best understood by reference to the figures. The following description is intended only by way of example, and simply illustrates certain example embodiments.

FIG. 1 illustrates an example pipe inspection robot 10 that may be utilized for capturing pipe inspection data, including water quality data. For purposes of clarity, a partially exploded view of the pipe inspection robot 10 is shown in FIG. 1. As explained in more detail hereinafter, the pipe inspection robot 10 may be utilized to navigate, explore, map, etc., various environments (e.g., water pipes, sewer pipes, etc.). In an embodiment, the pipe inspection robot 10 may be implemented as an autonomous mobile robot 10 utilized for pipe inspection (e.g., of a sewer pipe). However, it will be appreciated that the pipe inspection robot 10 may be embodied in any number of different types of inspection platforms, including non-autonomous devices and platforms, and may be utilized in a plurality of other environments.

The autonomous mobile robot 10 used by way of example for descriptive purposes includes a sensor component 12 and a chassis portion 14. The sensor component 12 is electrically and mechanically connected to the chassis portion 14. As shown in FIG. 1, the autonomous mobile robot 10 may also include a riser portion 16 which is positioned between the sensor component 12 and the chassis portion 14, and is electrically and mechanically connected to each. The riser portion 16 operates to increase the distance the sensor component 12 is situated above the lowest portion of the pipe, and may be utilized in large pipe applications to provide a desired vantage point for various sensing devices of the sensor component 12. Additionally, riser portion 16 and sensor component 12 are modular, i.e., they may be coupled/decoupled to and from the autonomous mobile robot 10. For example, according to other embodiments, the autonomous mobile robot 10 does not include the above-described riser portion 16. Functionality of the autonomous mobile robot 10 may be implemented by a computing device and/or a computer program stored on a computer-readable medium, as further described herein.

According to an embodiment, the sensor component 12 includes a plurality of sensing devices (e.g., a camera, a radar device, a sonar device, an infrared device, a laser device, etc.) for sensing the conditions within the environment, a computing device communicably connected to the sensing devices and having a processor for processing raw information captured by the sensing devices, a memory device communicably connected to a computing device for storing the raw and/or processed information, and control circuitry communicably connected to the computing device for controlling various components of the autonomous mobile robot 10. The memory device may also be utilized to store software that is utilized by the autonomous mobile robot 10 to navigate, explore, map, etc., the environment.

As further shown in FIG. 1, the chassis portion 14 includes a first track 18, and a second track 20. In an embodiment, the first track 18 is identical to the second track 20. The first and second tracks 18, 20 may be fabricated from any suitable material or combination of materials. The first and second tracks 18, 20 each define a plurality of openings 22 there-through. The openings 22 may be of any suitable shape and size, and may be arranged in any suitable configuration. Although only two rows of the openings 22 are shown in FIG. 1 for each track, it is understood that the openings 22 may be arranged in any number of rows. The first track 18 is positioned adjacent the second track 20. Collectively, the first and second tracks 18, 20 define a spacing there-between, and cover substantially the entire width of the chassis portion 14. For example, according to an embodiment, the width of the chassis portion is approximately 100 millimeters, and the first and second tracks 18, 20 collectively cover approximately 92 of the 100 millimeters.

The first track 18 defines a first surface 18a and a second surface (not shown in FIG. 1) opposite the first surface 18a. According an embodiment, the first surface 18a is the surface that comes into contact with an interior surface of a pipe when the autonomous mobile robot 10 is being utilized for a pipe application. The first surface 18a of the first track 18 is substantially smooth. Similarly, the second track 20 defines a first surface 20a and a second surface (not shown in FIG. 1) opposite the first surface 20a. The first surface 20a is the surface that comes into contact with an interior surface of a pipe when the autonomous mobile robot 10 is being utilized for a pipe application. Again, the first surface 20a of the first track 20 may be substantially smooth. The respective first surfaces 18a, 20a of the first and second tracks 18, 20 have a relatively high static coefficient of friction.

The first and second tracks 18, 20 may be referred to as full coverage/wide tracks. Due to the collective width of the first and second tracks 18, 20 relative to the width of the chassis portion 14, the first and second tracks 18, 20 collectively form nearly the entire "front," "bottom" and "rear" surfaces of the chassis portion 14. Thus, when the autonomous mobile robot 10 encounters any debris or feature within the sewer pipe, the first surfaces 18a, 20a of the first and second tracks 18, 20 come into contact with the debris or feature. In contrast to wheeled robots and narrow track robots, the full coverage/wide tracks 18, 20 are configured to enable the autonomous mobile robot 10 to climb over the debris or feature and continue performing the inspection, navigation, mapping, etc. Additionally, nearly all of the weight of the autonomous mobile robot 10 passes through the moving full coverage/wide tracks 18, 20 to the encountered debris or feature. Therefore, the autonomous mobile robot 10 is configured to always continue driving as the full coverage tracks 18, 20 cannot rotate without contacting something to react with and continue driving.

As further illustrated in FIG. 1, in an embodiment the autonomous mobile robot 10 may comprise one or more water quality probes 24. The water quality probe 24 illustrated in FIG. 1 is mounted to sensor component 12 by way of an extension piece 26. The extension piece 26 attaches to an attachment port 28 on the water quality probe 24. The extension piece 26 permits power and data connection for communications between the water quality probe 24 and the sensor component 12, and in turn possibly to the chassis portion 14, as further described herein.

The water quality probe 24 may be maintained in a fixed position with respect to the sensor component 12; however, in an embodiment, the water quality probe 24 may be repositioned by pivoting about the connection offered by the interface of port 28 and extension piece 26, as illustrated by the double headed arrow in FIG. 1. This permits an end of the water quality probe 24 to be repositioned closer to the ground or water surface, e.g., as the autonomous mobile robot 10 moves through a pipe.

Referring to FIG. 1 and FIG. 2(A-B), the water quality probe 24 may be repositioned by inclusion of an electric motor 32 housed within the water quality probe 24 and configured to rotate the water quality probe about the connection offered by the interface of port 28 and extension piece 26.

In an embodiment, power for the electric motor 32 of water quality probe 24 may be provided by a battery housed within the sensor component 12 and connected by wire to water quality probe 24 by extension piece 26. Similarly, control data may be communicated to electric motor 32 of water quality probe 24 by a wired connection between sensor component 12 and water quality probe 24, although the control data may be communicated using wireless communication as well. In an embodiment, the water quality probe 24 may be repositioned by an operator that communicates control instructions, whether through wired connection to sensor component 12 or via wireless communication to sensor component 12, such that an operator may remotely control the positioning and activation of water quality probe 24. Alternatively, water quality probe 24 may be provided in a fixed position, pointed downward, such that the sensor end 30 of the water quality probe 24 comes into contact with water or fluid, e.g., proximate to the autonomous mobile robot's 10 tracks.

Illustrated in FIG. 2A is a water quality probe 24 that may be reversibly attached to an autonomous mobile robot 10, e.g., via attachment to sensor component 12. The water quality probe 24 includes port 28 for power and data connection, as well as mechanical coupling to another component (e.g., sensor component 12 of FIG. 1). The water quality probe 24 includes a sensing part or end 30, which may comprise one or more water quality sensors.

By way of example, sensing part 30 may be formed of pH sensitive glass or other ion sensitive material and filled with a buffer solution that bathes an internal electrode. Other pH probe components may be included in water quality probe 24, such as a reference electrode and circuitry or meter electronics 38 coupling a pH electrode and a reference electrode, as will be understood by those having ordinary skill in the art.

Additional or alternative components may be included in the water quality probe 24, e.g., depending on the types of measurements that are to be obtained. For example, if ORP measurements are to be obtained, patch or foil metallic electrodes may be provided on the surface of probe at end 30 for conducting ORP measurements. Likewise, other sensor components may be included in water quality probe 24 such that the water quality probe 24 is a combination sensor. In an embodiment, more than one water quality probe 24 may be attached to the sensor component 12, e.g., a second water quality probe 24 may be attached to the opposite side of the sensor component 12. If more than one water quality probe 24 is provided, these may be operated in a cooperative manner or independently.

Referring now to FIG. 2B, a cross section of an end of the water quality probe 24 is illustrated. As shown, an electric motor 32 is provided proximate to the port 28 of water quality probe 24. This permits the electric motor 32 to be powered and controlled by power 34 and data 36 lines, here illustrated exiting the rear of the water quality probe 24, although these may be routed through port 28 and extension piece 26, as described herein. The electric motor 32 causes the water quality probe 24 to reposition, as described herein.

Further, water quality probe includes circuitry 38 and connection 40 for operating the sensor part 30 of water quality probe 24 to obtain water quality measurements. For example, in the case of a pH measuring water quality probe 24, the circuitry 38 may include meter electronics and memory having a program of instructions for obtaining voltage measurements from a measuring electrode and a reference electrode connected to circuitry 38 by connection 40. The circuitry 38 may directly report the measurements using data lines 36a, 36 or may process the measurements and report pH readings via data lines 36a, 36. The operation of circuitry 38 may be controlled, e.g., by communication by or through sensor component 12, for example communicated via data line 36, 36a.

An embodiment thus is capable of producing real time water quality measurements using an autonomous mobile robot 10 including a water quality probe 24 in addition to other sensors included in a sensor component 12. An example of obtaining and reporting water quality measurements is provided in FIG. 3.

Figure 3:
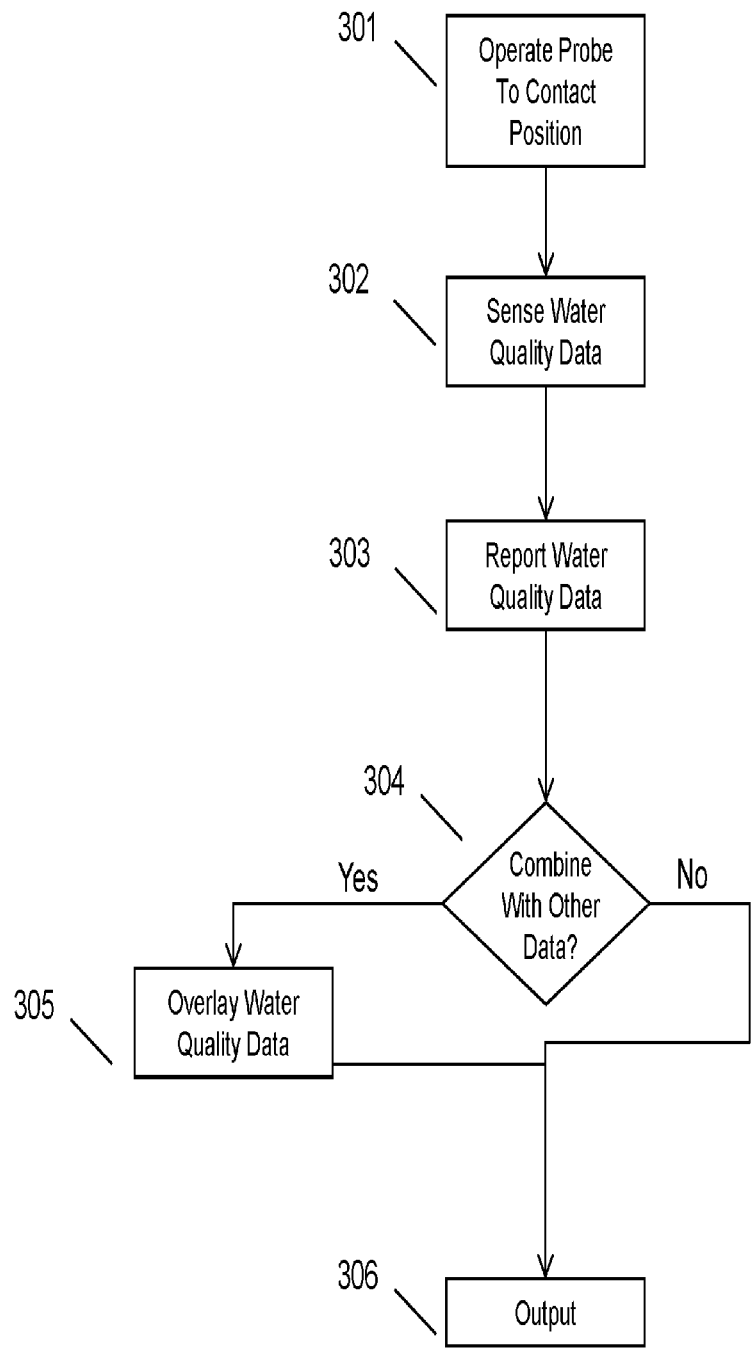
FIG. 3 illustrates an example method of collecting in-pipe water quality data using a mobile pipe inspection robot.

As illustrated in FIG. 3, an autonomous mission may be loaded into sensor component 12 ahead of time, or, an operator may provide mission details or other controls in real time to sensor component 12 or to other on-board component which contains a memory and a processor, e.g., chassis portion 14. If indicated by the mission or if instructed by an operator in real time, mobile inspection robot operates the water quality probe at 301 to a contact position such that a sensor end, e.g., end 30, of the water quality probe contacts the fluid to be tested. Again, the water quality probe may be manually positioned into a contact position or mounted at a fixed position that promotes contact with fluid within the pipe as the autonomous mobile inspection robot traverses the pipe's interior.

At 302, the water quality probe is in contact with the fluid in question and may sense water quality data, e.g., detect relative voltage or potential of the fluid as compared to a reference solution included in the water quality probe for the purpose of pH sensing. The timing of the measurement or sensing of the water quality data may be likewise controlled, e.g., as part of a pre-programmed mission, in response to an operator control, a combination of the foregoing, etc.

The water quality data may then be reported by the water quality probe, the sensor component, or a combination thereof, as indicated at 303. As has been described herein, the water quality data may be reported at 303 in response to a trigger, such as a request for sensing or a request for reporting of water quality data, or as part of a program, e.g., according to a predetermined schedule or as a stream of data. The reporting of the water quality data at 303 may be considered as a local reporting, e.g., the water quality data being sent from the water quality probe to a local component, such as sensor component 12, or may be considered as a reporting to a remote device, e.g., an operator's laptop computer.

If the water quality data is to be combined with other sensed data, as determined at 304, the water quality data may be combined, e.g., overlaid with the other sensed data, as indicated at 305. For example, the water quality data may be combined with a video or laser scan of the pipe's interior. This video or laser scan data may comprise data forming a visual display image, where the video data or laser scan data of the pipe's interior is combined with the water quality data, e.g., as an overlay of text and/or graphics on the visual display image. This makes it possible for an operator to view in real time water quality data associated with what the operator is viewing. The combined data may be stored and viewed at a later time.

The combining of the data at 305 may be done prior to reporting or after reporting of the water quality data. For example, the water quality data may be overlaid locally by a component of the autonomous mobile robot, such as sensor component 12, and thereafter communicated to a remote device, e.g., an operator's laptop computing device. Alternatively, the water quality data may be reported ahead of time, e.g., with a time stamp, and later associated with corresponding video or laser scan data to form a composite image.

If no combination of water quality data is to be made with other sensed data, then the water quality data may simply be reported outbound from the autonomous mobile robot, as indicated at 306. If the water quality data is combined with the other sensed data locally, it may be output as combined data, also indicated at 306.

Figure 4:
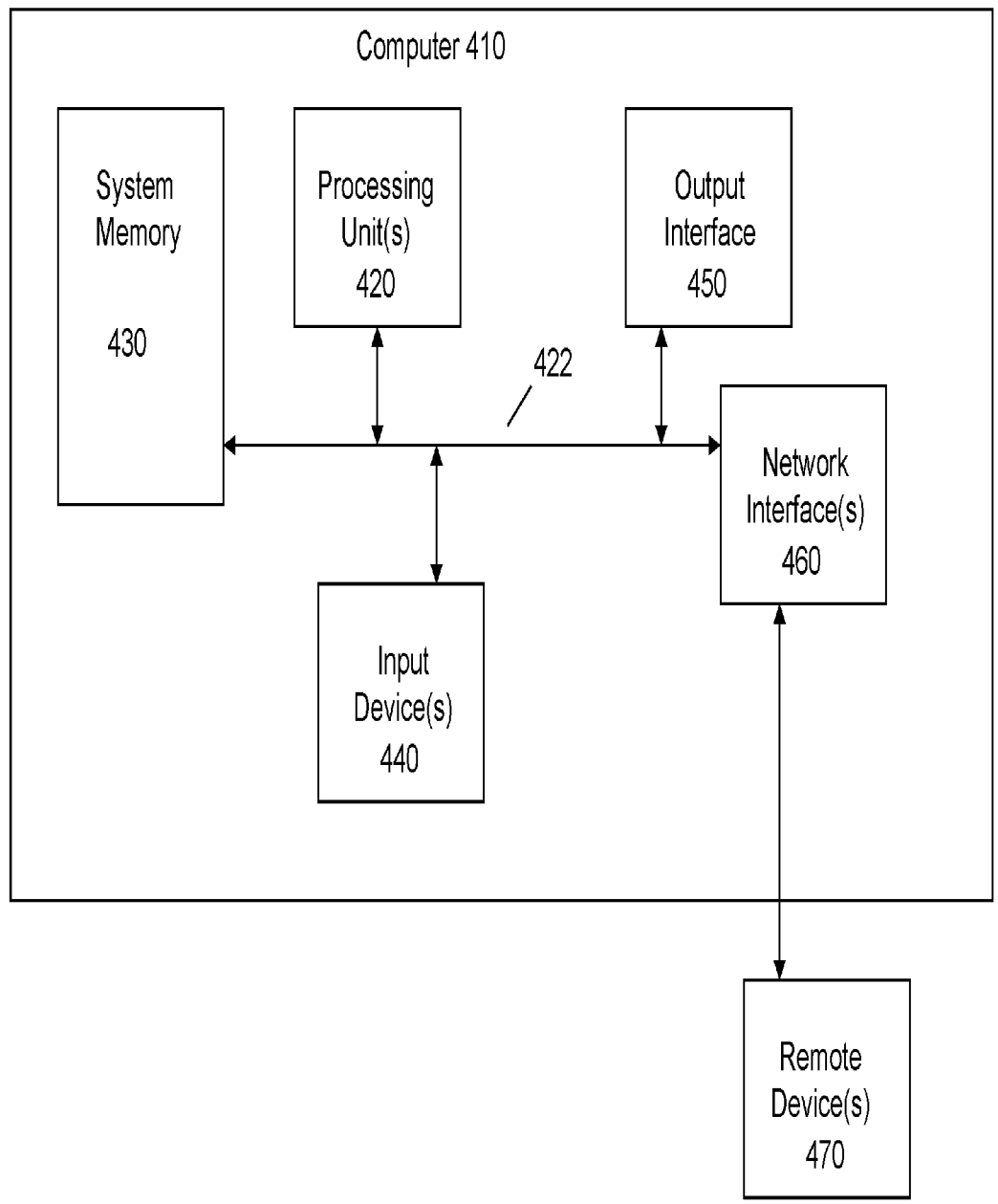
FIG. 4 illustrates an example of device electronics in the form of a computer.

It will be readily understood that certain embodiments can be implemented using any of a wide variety of devices or combinations of devices. Referring to FIG. 4, an example device that may be used in implementing one or more embodiments includes a computing device (computer) 410. In this regard, a computing device 410 may be operatively coupled to autonomous mobile robot 10 and provide hosted services (data storage, data analysis, data summary and querying, and the like). For example, computing device 410 may provide network-based access to autonomous mobile robot 10 for reporting water quality data, receiving data such as autonomous mission protocols, etc. Additionally, or alternatively, autonomous mobile robot 10 may incorporate a computing device such as outlined in FIG. 4, e.g., included on board in sensor component 12.

The computing device 410 may execute program instructions configured to store and analyze pipe segment data and perform other functionality of the embodiments, as described herein. Components of the computing device 410 may include, but are not limited to, a processing unit 420, a system memory 430, and a system bus 422 that couples various system components including the system memory 430 to the processing unit 420. The computer 410 may include or have access to a variety of computer readable media, for example for storing infrastructure data, inspection mission data, program routines for sensing water quality and other characteristics of a pipe interior, etc. The system memory 430 may include computer readable storage media in the form of volatile and/or nonvolatile memory such as read only memory (ROM) and/or random-access memory (RAM). By way of example, and not limitation, system memory 430 may also include an operating system, application programs, other program modules, and program data.

A user can interface with (for example, enter commands and information) the computing device 410 through input device(s) 440. A monitor or other type of device can also be connected to the system bus 422 via an interface, such as an output interface 450. In addition to a monitor, computers may also include other peripheral output devices. The computing device 410 may operate in a networked or distributed environment using logical connections to one or more other remote computers or databases (remote device(s) 470) via network interface(s) 460. The logical connections may include a network, such local area network (LAN) or a wide area network (WAN), but may also include other networks/buses.

As will be appreciated by one skilled in the art, various aspects may be embodied as a system, method or device program product. Accordingly, aspects may take the form of an entirely hardware embodiment or an embodiment including software that may all generally be referred to herein as a "circuit," "module" or "system." Furthermore, aspects may take the form of a device program product embodied in one or more device readable medium(s) having device readable program code embodied therewith.

It should be noted that the various functions described herein may be implemented using instructions stored on a device readable storage medium, such as a non-signal storage device, that are executed by a processor. A storage device may be, for example, an electronic, magnetic, optical, electromagnetic, infrared, or semiconductor system, apparatus, or device, or any suitable combination of the foregoing. More specific examples of a storage medium would include the following: a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a storage device is not a signal and "non-transitory" includes all media except signal media.

Program code embodied on a storage medium may be transmitted using any appropriate medium, including but not limited to wireless, wireline, optical fiber cable, RF, etc., or any suitable combination of the foregoing.

Program code for carrying out operations may be written in any combination of one or more programming languages. The program code may execute entirely on a single device, partly on a single device, as a stand-alone software package, partly on single device and partly on another device, or entirely on the other device. In some cases, the devices may be connected through any type of connection or network, including a local area network (LAN) or a wide area network (WAN), or the connection may be made through other devices (for example, through the Internet using an Internet Service Provider), through wireless connections, e.g., near-field communication, or through a hard wire connection, such as over a USB connection.

Example embodiments are described herein with reference to the figures, which illustrate example methods, devices and program products according to various example embodiments. It will be understood that the actions and functionality may be implemented at least in part by program instructions. These program instructions may be provided to a processor of a device to produce a special purpose machine, such that the instructions, which execute via a processor of the device implement the functions/acts specified.

It is worth noting that while specific blocks are used in the figures, and a particular ordering of blocks has been illustrated, these are non-limiting examples. In certain contexts, two or more blocks may be combined, a block may be split into two or more blocks, or certain blocks may be re-ordered or re-organized as appropriate, as the explicit illustrated examples are used only for descriptive purposes and are not to be construed as limiting.

As used herein, the singular "a" and "an" may be construed as including the plural "one or more" unless clearly indicated otherwise.

This disclosure has been presented for purposes of illustration and description but is not intended to be exhaustive or limiting. Many modifications and variations will be apparent to those of ordinary skill in the art. The example embodiments were chosen and described in order to explain principles and practical application, and to enable others of ordinary skill in the art to understand the disclosure for various embodiments with various modifications as are suited to the particular use contemplated.

Thus, although illustrative example embodiments have been described herein with reference to the accompanying figures, it is to be understood that this description is not limiting and that various other changes and modifications may be affected therein by one skilled in the art without departing from the scope or spirit of the disclosure.

What is claimed is:

1. A pipe inspection robot, comprising:
    a chassis configured to traverse through an interior of a water or sewer pipe;
    a water quality probe comprising a first end that couples to the chassis and a sensing end distal thereto; and
    an electric motor configured to reposition the sensing end of the water quality probe with respect to the chassis;
    said electric motor acting to move the sensing end of the water quality probe to reposition the sensing end proximate to fluid containing water located proximate to a bottom part of the chassis;
    the sensing end configured to contact the fluid containing water for contact sensing of water quality data.

2. The pipe inspection robot of claim 1, wherein the water quality data comprises one or more of pH data, oxidation reduction potential data, and metal ion sensing data.

3. The pipe inspection robot of claim 1, comprising a processor configured to:
    operate the water quality probe to collect the water quality data; and
    communicate the water quality data collected over a network connection.

4. The pipe inspection robot of claim 3, wherein the processor is further configured to time stamp the water quality data.

5. The pipe inspection robot of claim 3, wherein the processor is further configured to output the time stamped water quality data over the network connection.

6. The pipe inspection robot of claim 3, comprising one or more additional sensors; wherein the processor is further configured to combine the water quality data with other sensed data obtained by the one or more additional sensors.

7. The pipe inspection robot of claim 6, wherein: to combine the water quality data comprises overlaying the water quality data on the other sensed data.

8. The pipe inspection robot of claim 6, wherein the other sensed data is selected from video data, laser scan data, or sonar data.

9. The pipe inspection robot of claim 1, wherein the water quality probe comprises a plurality of water quality probes.

10. The pipe inspection robot of claim 1, wherein the water quality probe comprises a pH probe.

11. A method for obtaining water quality data for a fluid containing water within a pipe, comprising:
    positioning a pipe inspection robot within a pipe;
    collecting, using a water quality probe of the pipe inspection robot, water quality data;
    the collecting comprising operating an electric motor to reposition a sensing end of the water quality probe with respect to the robot;
    said electric motor acting to move the sensing end of the water quality probe to reposition the sensing end proximate to fluid containing water located proximate to a bottom part of the pipe inspection robot;
    the sensing end contacting the fluid containing water for contact sensing of water quality data; and
    communicating, over a network connection, the water quality data to a remote device.

12. The method of claim 11, wherein the water quality data comprises one or more of pH data, oxidation reduction potential data, and metal ion sensing data.

13. The method of claim 11, further comprising applying a time stamp to the water quality data.

14. The method of claim 13, further comprising outputting the time stamped water quality data over the network connection.

15. The method of claim 11, further comprising combining the water quality data with other sensed data obtained by the pipe inspection robot.

16. The method of claim 15, wherein: combining the water quality data comprises overlaying the water quality data on the other sensed data.

17. The method of claim 15, wherein the other sensed data obtained by the pipe inspection robot is selected from video data, laser scan data, or sonar data.

18. The method of claim 11, wherein the water quality probe comprises a plurality of water quality probes.

19. A pipe inspection robot, comprising:
    a chassis;
    a water quality probe coupled to the chassis;
    an electric motor that imparts movement to the water quality probe to reposition the water quality probe to a position that is closer to a bottom part of the chassis;
    wherein, in the position, a sensing end of the water quality probe is able to contact fluid comprising water located in a bottom of the pipe proximate to a bottom of the chassis; and
    a processor operatively coupled to the water quality probe;
    said processor configured to:
    operate the water quality probe to collect water quality data related to the fluid comprising water contained within the pipe; and
    communicate the water quality data collected over a network connection.

20. The pipe inspection robot of claim 19, comprising a sensor component having one or cameras disposed therein.

* * * * *